United States Patent [19]
Umeda

[11] Patent Number: 5,255,668
[45] Date of Patent: Oct. 26, 1993

[54] BENDING DEVICE

[75] Inventor: Hiroyuki Umeda, Saitama, Japan

[73] Assignee: Kabushiki Kaisha Machida Seisakusho, Tokyo, Japan

[21] Appl. No.: 854,912

[22] Filed: Mar. 20, 1992

[30] Foreign Application Priority Data

Apr. 8, 1991 [JP] Japan .................................. 3-103074

[51] Int. Cl.⁵ .............................................. A61B 1/00
[52] U.S. Cl. ...................... 128/4; 128/772; 604/95; 604/282
[58] Field of Search ............ 128/4, 6, 656, 657, 128/658, 772; 138/118; 604/95, 280, 282

[56] References Cited

U.S. PATENT DOCUMENTS

| | | | |
|---|---|---|---|
| 4,686,963 | 8/1987 | Cohen et al. | 128/4 |
| 5,002,041 | 3/1991 | Chikama | 128/4 |
| 5,106,381 | 4/1992 | Chikama | 128/772 X |
| 5,176,126 | 1/1993 | Chikama | 128/4 |

FOREIGN PATENT DOCUMENTS

| | | | |
|---|---|---|---|
| 10605 | 1/1980 | Japan | 128/4 |
| 143806 | 10/1980 | Japan | 128/4 |
| 79901 | 5/1988 | Japan | 128/4 |

Primary Examiner—Richard J. Apley
Assistant Examiner—Karen Jalbert
Attorney, Agent, or Firm—Fish & Richardson

[57] ABSTRACT

A bending device for use in an endoscope, a catheter or the like includes a bendable frame having a generally cylindrical shape as a whole, a tip member having a rear end portion whose outer peripheral surface is cylindrical, and a connecting tube interconnecting the frame and the tip member. A slit is formed through a front end portion of the connecting tube and extends axially of the connecting tube. A rear end of the slit is disposed rearwardly of a rear end of the tip member. An operating wire is passed axially through the frame and the connecting tube, and a front end portion of the operating wire is received in a receiving recess, defined by the slit of the connecting tube and the outer peripheral surface of the rear end portion of the tip member, and is fixedly secured to the connecting tube.

7 Claims, 2 Drawing Sheets

BENDING DEVICE

BACKGROUND OF THE INVENTION

This invention relates to a bending device used, for example, in an endoscope.

As is well known, an endoscope comprises a hollow body, a flexible insertion portion extending from a front end of this body, and a flexible bending portion extending from the distal end of the insertion portion. The bending portion has a tip member at its distal end. An inspection window and an illumination window are formed at the tip member. A manipulation member for remotely controlling the bending portion is provided at the body.

A bending device serving as an internal structure of the bending portion comprises a bendable frame of a cylindrical shape, the tip member provided forwardly of the frame, a connecting tube interconnecting the frame and the tip member, and operating wires. The frame comprises, for example, a number of juxtaposed rings rotatably connected to one another. The rear end portion of the operating wire is connected to the manipulation member, and the front end portion of the operating wire is connected to the connecting tube. With this arrangement, when the manipulation member is operated, an operating force is transmitted to the connecting tube via the operating wire to bend the frame so as to direct the inspection window and the illumination window of the tip member in a desired direction.

Conventionally, as shown in FIG. 1 of Japanese Laid-Open Utility Model Application No. 50-81696, the front end portion of the operating wire has been connected to the inner peripheral surface of the connecting tube by brazing or the like. In this case, however, the connecting position is not accurate, and the connecting strength is low. Further, the operating efficiency with respect to the brazing of the front end portion of the operating wire to the inner peripheral surface of the connecting tube is very low.

Therefore, Japanese Laid-Open Utility Model Application No. 55-143806 proposes an improvement in the connection of a front end portion of an operating wire. More specifically, a rear end portion of a connecting tube is deformed by pressing to be projected inwardly so as to form a mounting portion (designated by reference numeral 6 in FIGS. 3 to 5 of this publication), and the operating wire is inserted into this mounting portion, and is fixedly secured thereto by brazing or the like. In this case, the position of connection of the front end portion of the operating wire to the connecting tube is accurate, and the connecting strength is high. Further, since the operation of fixing the operating wire to the connecting tube can be done outside of the connecting tube, the operating efficiency with respect to the brazing or the like is high.

However, in the connecting method of the above Japanese Laid-Open Utility Model Application No. 55-143806, since the mounting portion is projected inwardly of the connecting tube, the internal space of the connecting tube through which optical fibers and etc., are passed is reduced. Therefore, to compensate for the loss of the internal space due to the provision of the mounting portion, the outer diameter of the connecting tube must be increased. This makes it difficult to meet the demand that the insertion portion and the bending portion should be reduced in diameter, and correspondingly the diameter of the connecting tube should be as small as possible, as in an endoscope for inspecting the interior of the bronchus. Further, the pressing operation can not be applied to the continuous tube of a small diameter, the reduction of the diameter of the connecting tube is limited.

Japanese Laid-Open Utility Model Application No. 63-79901 discloses an interesting manner of connection of a front end portion of an operating wire. More specifically, an axial groove 13 is formed in an outer peripheral surface of a rear end portion of a tip member 1. The front end portion of the operating wire 10 is received in this groove, and in this condition a connecting tube 7 is fitted on the rear end portion of the tip member, thereby connecting the front end portion of the operating wire to the tip member. In this case, the position of connection of the front end portion of the operating wire is accurate, and there is no need to increase the diameter of the connecting tube. However, as described above, in the case of the endoscope having the narrow insertion portion and bending portion, the operating wire is very thin, and therefore it is not easy to form the narrow groove, corresponding to such a thin operating wire, in the outer peripheral surface of the tip member, and to achieve this, an expensive machine is needed.

Reference is made to other prior art related to the present invention. Japanese Laid-Open Utility Model Application No. 55-10605 describes in FIG. 1 a bending device for an endoscope. This bending device comprises a single coil serving as a cylindrical frame, and a resilient thin plate. A series of juxtaposed engagement recesses are formed in each of the opposite side edges of the resilient thin plate in the longitudinal direction of this resilient thin plate, and a series of turn portions of the coil are engaged in the engagement recesses.

U.S. Pat. No. 4,686,963 discloses a bending device for an endoscope which comprises a series of rings jointly constituting a cylindrical frame, and a resilient thin plate. A pair of axial grooves are formed respectively in diametrically-opposite portions of the inner peripheral surface of each ring, and the opposite side edges of the resilient thin plate are received in the pair of grooves in each ring. A pair of grooves are also formed in diametrically-opposite portions of an inner peripheral surface of a tip member, and the opposite side edges of the front end portion of the resilient thin plate are received in these grooves, respectively, and the resilient thin plate is connected at its front end portion to the tip member against axial movement.

SUMMARY OF THE INVENTION

It is an object of this invention to provide a bending device in which a connecting tube can be reduced in diameter, and means for connecting a front end portion of an operating wire can be obtained by a simple processing.

According to the present invention, there is provided a bending device comprising:

(a) a bendable frame having a generally cylindrical shape as a whole;

(b) a tip member provided forwardly of the frame, the tip member having a rear end portion whose outer peripheral surface is cylindrical;

(c) a connecting tube of a cylindrical shape interconnecting the frame and the tip member, the rear end portion of the tip member being received in and fixed to a front end portion of the connecting tube, a slit being formed through the front end portion of the connecting tube and extending axially of the connecting tube, a rear end of the slit being disposed rearwardly of a rear end of the tip member, and a receiving recess being defined by the slit of the connecting tube and the outer peripheral surface of the rear end portion of the tip member; and (d) an operating wire for receiving an operating force at its rear end so as to bend the frame, the operating wire passing axially through the frame and the connecting tube, a front end portion of the operating wire being received in the receiving recess and fixedly secured to the connecting tube.

DESCRIPTION OF THE PREFERRED EMBODIMENT

Figure 1:
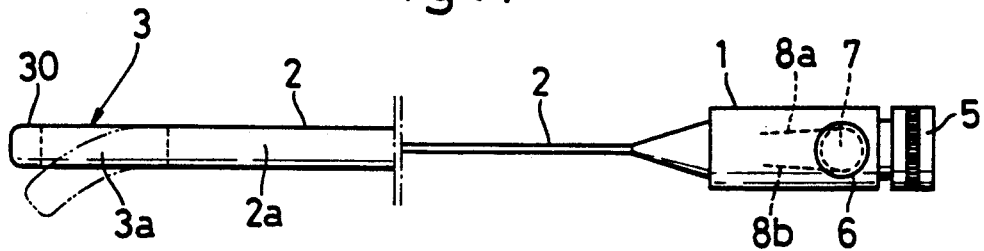
FIG. 1 is a partly enlarged, front-elevational view of an endoscope having a bending device of the present invention.
Figure 2:
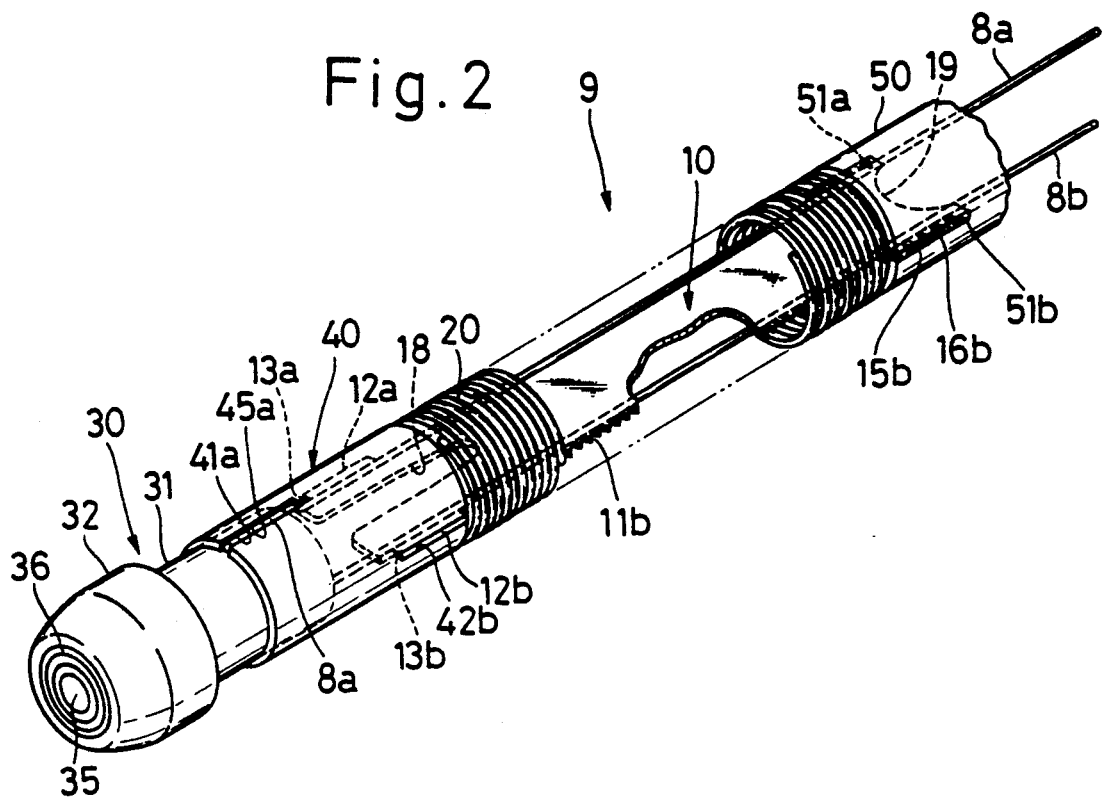
FIG. 2 is an enlarged perspective view of the bending device.

FIG. 1 shows an endoscope used, for example, for inspecting the interior of the bronchus. This endoscope comprises a hollow body 1, an insertion portion 2 extending from the front end of the body 1, and a bending portion 3 extending from the distal end of the insertion portion 2. Each of the insertion portion 2 and the bending portion 3 has a cylindrical shape, and is so flexible as to be bent, and is much thinner or smaller in diameter (for example, about 2 mm), as compared with those of an endoscope of the general type. In FIG. 1, the distal end portion of the insertion portion 2 and the bending portion 3 are shown on an enlarged scale for better understanding.

An ocular tube 5 is mounted on the rear end of the body 1. One end of a cable (not shown) is fixedly secured to the side wall of the body 1, and a connector (not shown) releasably connected to a light source device is connected to the other end of this cable. A manipulation dial 6 for remotely controlling the bending portion 3 is mounted on the side wall of the body 1. A pulley 7 is mounted within the body 1, and is connected to the manipulation dial 6 via a shaft (not shown) extending through the side wall of the body 1. Two operating wires 8a and 8b are fixedly secured at their rear end portions to the peripheral surface of the pulley 7. The two operating wires 8a and 8b extend forwardly from the upper and lower portions of the pulley 7, respectively.

The bending portion 3 has, as its internal structure, a bending device 9 shown in FIGS. 2 to 5. The bending device 9 comprises the above-mentioned operating wires 8a and 8b, an elongate resilient thin plate 10, a coil (frame) 20 wound on the resilient thin plate 10, a tip member 30 disposed forwardly of the coil 20, a front connecting tube 40 interconnecting the front end of the coil 20 and the tip member 30, and a rear connecting tube 50 interconnecting the rear end of the coil 20 and the internal structure of the insertion portion 2. Each of the front and rear connecting tubes 40 and 50 has a cylindrical shape, and the outer diameter of each of these tubes 40 and 50 is generally equal to the outer diameter of the coil 20, and is slightly smaller than 2 mm. The thickness of the peripheral wall of each of the connecting tubes 40 and 50 is generally equal to the diameter of a wire constituting the coil 20, and is 0.1 mm. The diameter of each of the operating wires 8a and 8b is about 0.09 mm.

The tip member 30 has a cylindrical body 31, and a head 32 extending from the front end of the body 31, the head 32 being greater in diameter than the body 31. An inspection window 35, as well as an illumination window 36 disposed in surrounding relation to the inspection window 35, is formed at the distal end face of the head 32. The ocular portion 5 is optically connected to the inspection window 35 via an image guide (not shown) including an optical fiber bundle passing through the body 1, the insertion portion 2 and the bending portion 3. With this arrangement, observation can be made from the ocular portion 5. Illumination light from the light source device is supplied to the illumination window 36 via a light guide including an optical fiber bundle passing through the above connector, the above cable, the body 1, the insertion portion 2 and the bending portion 3.

A pair of slits 41a and 41b are formed respectively through diametrically-opposite portions of the front end portion of the front connecting tube 40, the slits 41a and 41b extending axially a predetermined distance from the front end of the connecting tube 40. The slits 41a and 41b are used for connecting the front end portions of the operating wires 8a and 8b, as later described. The width of the slits 41a and 41b is generally equal to or slightly greater than the diameter of the operating wires 8a and 8b. Another pair of slits 42a and 42b are also formed respectively through diametrically-opposite portions of the rear end portion of the connecting tube 40, the slits 42a and 42b extending axially a predetermined distance from the rear end of the connecting tube 40. The slits 41a and 41b are circumferentially spaced 90° from the slits 42a and 42b, respectively. The slits 42a and 42b are used for connecting the front end portion of the resilient thin plate 10 as later described. The width of the slits 42a and 42b is generally equal to or slightly greater than the thickness of the resilient thin plate 10.

The rear end portion of the body 31 of the tip member 30 is inserted into the front end portion of the connecting tube 40, and is fixedly connected thereto by an adhesive. In this connected condition, the rear ends of the slits 41a and 41b of the connecting tube 40 are disposed rearwardly of the rear end of the tip member 30. A receiving recess 45a is defined by the front end portion of the slit 41a and the outer peripheral surface of the rear end portion of the body 31 of the tip member 30, and similarly a receiving recess 45b is defined by the front end portion of the slit 41b and the outer peripheral surface of the rear end portion of the body 31.

A pair of slits 51a and 51b are formed respectively through diametrically-opposite portions of the front end portion of the rear connecting tube 50, the slits 51a and 51b extending axially a predetermined distance from the front end of the connecting tube 50. The slits 51a and 51b are used for connecting the rear end portion of the resilient thin plate 10. The width of the slits 51a and 51b is generally equal to or slightly greater than the thickness of the resilient thin plate 10.

Figure 3:
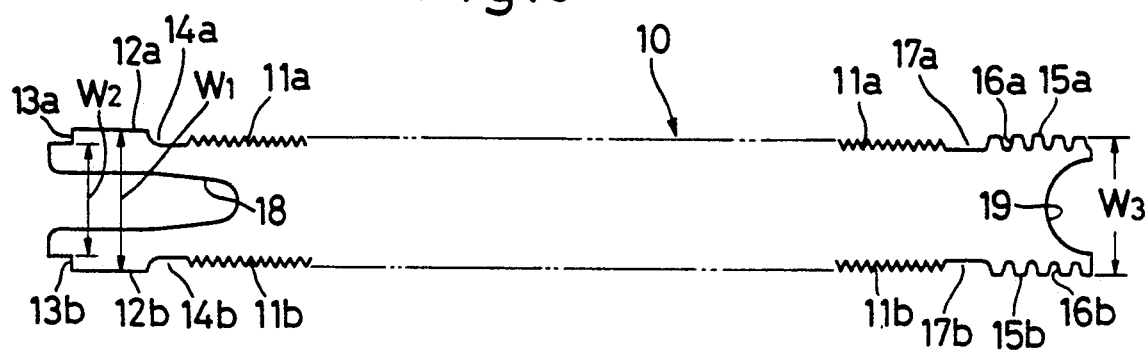
FIG. 3 is a top plan view of a resilient thin plate used in the bending device.
Figure 4:
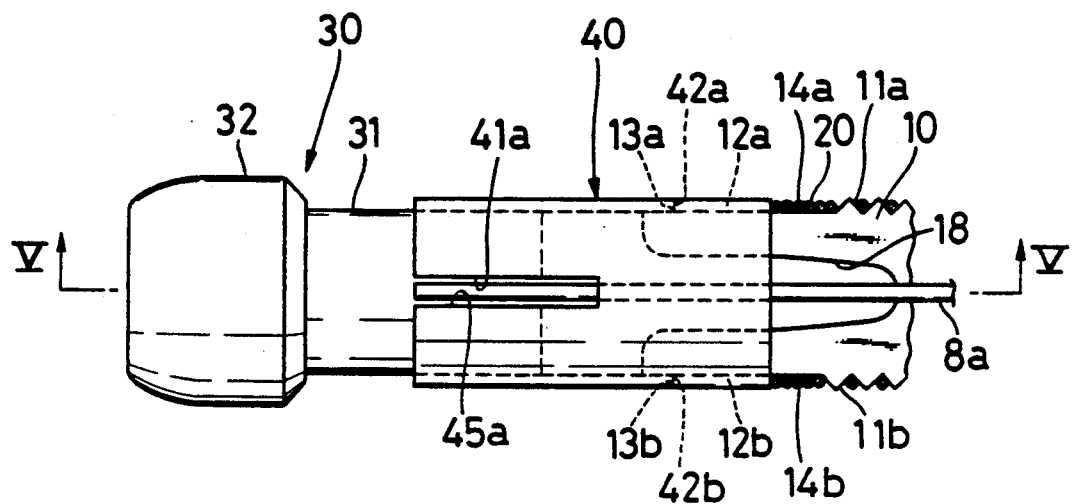
FIG. 4 is an enlarged top plan view of a distal end portion of the bending device.
Figure 5:
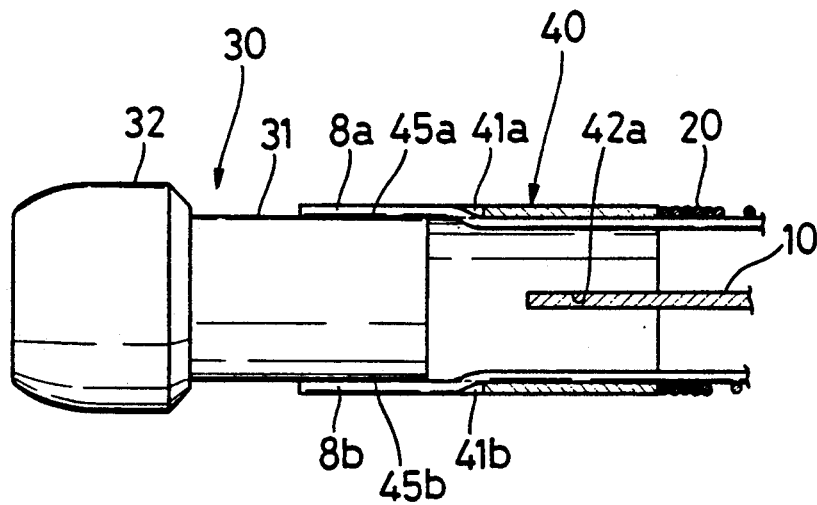
FIG. 5 is a cross-sectional view taken along the line V—V of FIG. 4.

The resilient thin plate 10 comprises, for example, a rolled steel sheet. The resilient thin plate 10 is completely flat throughout the length thereof, and does not have any bent portion. As best shown in FIG. 3, except for the opposite end portions of the resilient thin plate 10, the opposite side edges of the resilient thin plate 10 are serrated to provide two series of engagement recesses 11a and 11b of a triangular shape, respectively. The coil 20 is engaged in the engagement recesses 11a and 11b.

A pair of engagement projections 12a and 12b are formed on and extend respectively from the opposite side edges of the front end portion of the resilient thin plate 10 in the direction of the width thereof. The length of the engagement projections 12a and 12b is generally equal to the length of the slits 42a and 42b. The width $W_1$ of that portion of the resilient thin plate 10 including the engagement projections 12a and 12b is generally equal to the outer diameter of the connecting tube 40. The opposite side edges of the foremost portion of the resilient thin plate 10 are notched, and the width $W_2$ of this foremost portion is generally equal to the inner diameter of the connecting tube 40. A step or shoulder 13a is formed on one side edge of the resilient thin plate 10, and is disposed between the foremost portion and the engagement projection 12a, and similarly a step 13b is formed on the other side edge of the resilient thin plate 10, and is disposed between the foremost portion and the engagement projection 12b. A receiving recess 14a is formed in the one side edge of the thin resilient plate 10, and is disposed between the engagement projection 12a and the foremost engagement recess 11a, and similarly a receiving recess 14b is formed in the other side edge of the thin resilient plate 10, and is disposed between the engagement projection 12b and the foremost engagement recess 11b.

Engagement projections 15a and 15b are formed on and extend respectively from the opposite side edges of the rear end portion of the resilient thin plate 10 in the direction of the width thereof. The length of the engagement projections 15a and 15b is generally equal to the length of the slits 51a and 51b of the rear connecting tube 50. The width $W_3$ of that portion of the resilient thin plate 10 including the engagement projections 15a and 15b is generally equal to the outer diameter of the rear connecting tube 40. A plurality of guide recesses 16a are formed in the engagement projection 15a, and are juxtaposed in the longitudinal direction of the resilient thin plate 10. Similarly, a plurality of guide recesses 16b are formed in the engagement projection 15b, and are juxtaposed in the longitudinal direction of the resilient thin plate 10. The guide recesses 16a and 16b serve to guide the coil 20. A receiving recess 17a is formed in the one side edge of the resilient thin plate 10, and is disposed between the engagement projection 15a and the rearmost engagement recess 11a, and similarly a receiving recess 17b is formed in the other side edge of the resilient thin plate 10, and is disposed between the engagement projection 15b and the rearmost engagement recess 11b.

Notches 18 and 19 for allowing the passage of the above-mentioned image guide and light guide therethrough are formed in the opposite ends of the resilient thin plate 10, respectively.

The coil 20 is wound on the resilient thin plate 10 in the following manner. The turn portions of the front end portion of the coil 20 are engaged in the guide recesses 16a and 16b, and then the coil 20 is rotated about its axis, so that the coil 20 is moved toward the front end of the resilient thin plate 10. Finally, each of those turn portions (annular portions) of the coil 20 intermediate the opposite end portions of the coil 20 is engaged in a respective one of the pairs of opposite engagement recesses 11a and 11b each of which pairs of recesses 11a and 11b are disposed generally in registry with each other in the direction of the width of the resilient thin plate 10. Therefore, the turn portions of the coil 20 intermediate the opposite end portions thereof are held spaced from one another at predetermined intervals. The turn portions of the front end portion of the coil 20 are received in the receiving recesses 14a and 14b of the resilient thin plate 10, and are wound tightly, and therefore are held in contact with one another. The turn portions of the rear end portion of the coil 20 are received in the receiving recesses 17a and 17b of the resilient thin plate 10, and are wound tightly, and therefore are held in contact with one another.

The front end portion of the resilient thin plate 10 is connected to the rear end portion of the connecting tube 40. More specifically, the engagement projections 12a and 12b of the resilient thin plate 10 are received in the slits 42a and 42b of the connecting tube 40, respectively, and the steps 13a and 13b of the resilient thin plate 10 abut against the front ends of the slits 42a and 42b, respectively, and the bifurcated foremost portion of the resilient thin plate 10 is substantially held in contact with the inner peripheral surface of the connecting tube 40. Therefore, the front end portion of the resilient thin plate 10 is accurately positioned in the circumferential, axial and radial directions of the connecting tube 40. In this condition, the engagement projections 12a and 12b are brazed to the connecting tube 40 from the outside of the connecting tube 40, and are fixed thereto.

The rear end portion of the resilient thin plate 10 is connected to the front end portion of the connecting tube 50. More specifically, the engagement projections 15a and 15b of the resilient thin plate 10 are received in the slits 51a and 51b of the connecting tube 50, and the rear ends of these projections 15a and 15b abut against the rear ends of the slits 51a and 51b, respectively. In this condition, the engagement projections 15a and 15b are fixedly secured to the connecting tube 50 by brazing or the like.

The front end of the coil 20 is abutted against and brazed to the rear end of the connecting tube 40. The rear end of the coil 20 is abutted against and brazed to the front end of the connecting tube 50. A retaining coil (not shown), which is formed by a strip and serves as the internal structure of the insertion tube 2, is connected at its front end portion to the rear end portion of the connecting tube 50. The rear end portion of the retaining coil is fixedly secured to the body 31.

The pair of operating wires 8a and 8b are extended from the body 31, and are passed respectively through a pair of guide coils mounted within the insertion portion 2, and are further passed through the coil 20 of the bending portion 3. The interior of the coil 20 is divided by the resilient thin plate 10 into a pair of space portions, and the pair of operating wires 8a and 8b are passed through the pair of space portions, respectively. The operating wires 8a and 8b extend axially near the inner peripheral surfaces of the connecting tube 50, the coil 20 and the connecting tube 40, and the front end portions of these wires 8a and 8b are received respectively in the receiving recesses 45a and 45b which are defined by the outer peripheral surface of the tip member 30 and the slits 41a and 41b. The front end portions of the operating wires 8a and 8b are fixedly secured to the connecting tube 40, for example, by brazing applied from the outside of the connecting tube 40.

The operation of fixing the front end portions of the operating wires 8a and 8b to the connecting tube 40 may be effected before or after the tip member 30 is inserted into and fixed to the connecting tube 40.

The insertion portion 2 comprises a braid (not shown) fitted on the above-mentioned retaining coil, and a tube 2a (shown only in FIG. 1) of a resin or rubber fitted on this braid.

The bending portion 3 comprises a braid which is softer than the braid of the insertion portion 2 and is fitted on the coil 20, the connecting tubes 40 and 50 and the body 31 of the tip member 30, and a tube 3a (shown only in FIG. 1) which is softer than the tube 2a of the insertion portion 2 and is fitted on the above braid of the bending portion 3.

In the above construction, since the bending portion 3 has the resilient thin plate 10, the bending portion 3 can be bent in a direction perpendicular to the plane of the resilient thin plate 10, that is, upwardly and downwardly in FIG. 1. When the manipulation dial 6 is angularly moved in a counterclockwise direction in FIG. 1, the operating wire 8b is pulled whereas the operating wire 8a is loosened. As a result, the bending portion 3 is bent or curved downwardly in FIG. 1. In contrast, when the manipulation dial 6 is angularly moved in a clockwise direction in FIG. 1, the bending portion 3 is curved upwardly.

In the bending device 9 of the above construction, the front end portions of the operating wires 8a and 8b are received in the receiving recesses 45a and 45b defined by the outer peripheral surface of the body 31 of the tip member 30 and the slits 41a and 41b of the connecting tube 40, and are fixed to the connecting tube 40. Therefore, any mounting portion for the operating wires 8a and 8b does not need to be provided inwardly of the connecting tube 40, and a sufficient internal space for accommodating the image guide and the light guide can be secured. In other words, the diameter of the connecting tube 40 can be reduced. The slits 41a and 41b and the slits 42a and 42b in the connecting tube 40, as well as the slits 51a and 51b in the connecting tube 50, can be easily formed, for example, by a disk-shaped whetstone rotating at high speed. The slits 41a and 41b, 42a and 42b, 51a and 51b may be formed by laser beam machining or electric discharge machining.

The present invention is not limited to the above embodiment, and various modifications can be made. For example, the slits, which receives the front end portions of the operating wires, respectively, may terminate short of the front end of the front connecting tube. The opposite ends of the coil may not be connected directly to the front and rear connecting tubes, respectively, in which case the coil is connected indirectly to the connecting tubes via the resilient thin plate. The number of the operating wires may be one or four. The frame may be constituted by a number of rings separate from one another, in which case these rings are engaged with the opposite side edges of the resilient thin plate. Also, the frame may be constituted by a number of juxtaposed rings rotatably connected to one another, in which case the use of the resilient thin plate is omitted. The bending device of the present invention can be applied also to a medical catheter.

What is claimed is:

1. A bending device comprising:

(a) a bendable frame having a generally cylindrical shape as a whole;

(b) a tip member provided forwardly of said frame, said tip member having a rear end portion whose outer peripheral surface is cylindrical;

(c) a connecting tube of a cylindrical shape interconnecting said frame and said tip member, the rear end portion of said tip member being received in and fixed to a front end portion of said connecting tube, a slit being formed through the front end portion of said connecting tube and extending axially of said connecting tube, a rear end of said slit being disposed rearwardly of a rear end of said tip member, and a receiving recess being defined by said slit of said connecting tube and the outer peripheral surface of the rear end portion of said tip member; and (d) an operating wire for receiving an operating force at its rear end so as to bend said frame, said operating wire passing axially through said frame and said connecting tube, a front end portion of said operating wire being received in said receiving recess and fixedly secured to said connecting tube.

2. A bending device according to claim 1 in which said operating wire has a diameter not larger than the thickness of a peripheral wall of said connecting tube, so that the front end portion of said operating wire received in said receiving recess is not projected from an outer peripheral surface of said connecting tube.

3. A bending device according to claim 1 in which said slit extends a predetermined distance from a front end of said connecting tube.

4. A bending device according to claim 1, in which there is provided a second operating wire, a second slit being formed through the front end portion of said connecting tube and extending axially of said connecting tube, said second slit being disposed in diametrically opposite relation to said first-mentioned slit, a second receiving recess being defined by said second slit of said connecting tube and the outer peripheral surface of the rear end portion of said tip member, and a front end portion of said second operating wire being received in said second receiving recess and fixedly secured to said connecting tube.

5. A bending device according to claim 1, in which there is provided an elongate resilient thin plate, said frame having annular portions juxtaposed axially of said resilient thin plate, said annular portions engaging opposite side edges of said resilient thin plate, a pair of second slits being formed through a rear end portion of said connecting tube and extending axially from a rear end of said connecting tube, said pair of second slits being circumferentially spaced about 90° from said first-mentioned slit, and being disposed in diametrically opposite relation to each other, said resilient thin plate having a pair of engagement projections extending respectively from the opposite side edges of a front end portion thereof in a direction of the width of said resilient thin plate, and said pair of engagement projections being fixedly received in said pair of second slits, respectively.

6. A bending device according to claim 5 in which said frame comprises a coil having juxtaposed turn portions which define said annular portions, respectively, a series of engagement recesses being formed in each of the opposite side edges of said resilient thin plate in a longitudinal direction of said resilient thin plate, each of said turn portions of said coil being received in a respective one of pairs of said opposite engagement recesses in the opposite side edges of said resilient thin plate each of which pairs of opposite engagement recesses are disposed generally in registry with each other in the direction of the width of said resilient thin plate, so that said juxtaposed turn portions are spaced a predetermined distance from one another, the outer diameter of said coil, as well as the width of the front end portion of the resilient thin plate including said engagement projections, being generally equal to the outer diameter of said connecting tube, and the diameter of a wire constituting said coil being generally equal to the thickness of a peripheral wall of said connecting tube.

7. A bending device according to claim 6, in which a foremost portion of said resilient thin plate is notched at its opposite side edges, and has a width generally equal to the inner diameter of said connecting tube, a step being formed at each of the opposite side edges of said resilient thin plate and disposed between the foremost portion of said resilient thin plate and a respective one of said pair of engagement projections, said steps being abutted against front ends of said pair of second slits, respectively.

* * * * *